United States Patent
Chaiken et al.

(10) Patent No.: US 7,050,842 B2
(45) Date of Patent: May 23, 2006

(54) METHOD OF TISSUE MODULATION FOR NONINVASIVE MEASUREMENT OF AN ANALYTE

(75) Inventors: Joseph Chaiken, Fayetteville, NY (US); Karen P. Peterson, Potomac, MD (US); Charles M. Peterson, Potomac, MD (US)

(73) Assignee: LighTouch Medical, Inc., Bryn Athyn, PA (US)

( * ) Notice: Subject to any disclaimer, the term of this patent is extended or adjusted under 35 U.S.C. 154(b) by 446 days.

(21) Appl. No.: 10/332,748

(22) PCT Filed: Jul. 11, 2001

(86) PCT No.: PCT/US01/22012

§ 371 (c)(1),
(2), (4) Date: Jan. 13, 2003

(87) PCT Pub. No.: WO02/03857

PCT Pub. Date: Jan. 17, 2002

(65) Prior Publication Data

US 2003/0208169 A1    Nov. 6, 2003

Related U.S. Application Data

(60) Provisional application No. 60/220,144, filed on Jul. 11, 2000.

(51) Int. Cl.
*A61B 5/00* (2006.01)
(52) U.S. Cl. ........................ 600/316; 600/322
(58) Field of Classification Search ............. 600/310, 600/316, 317, 322, 323, 326, 330, 335, 336, 600/476
See application file for complete search history.

(56) References Cited

U.S. PATENT DOCUMENTS

| | | | |
|---|---|---|---|
| 4,169,676 A | 10/1979 | Kaiser | |
| 4,655,225 A | 4/1987 | Dahne et al. | |
| 4,890,619 A | 1/1990 | Hatschek | |
| 5,086,229 A | 2/1992 | Rosenthal et al. | |
| 5,159,929 A | 11/1992 | Morris et al. | |
| 5,370,114 A | 12/1994 | Wong et al. | |
| 5,372,135 A | 12/1994 | Mendelson et al. | |
| 5,510,894 A | 4/1996 | Batchelder et al. | |
| 5,551,422 A | 9/1996 | Simonsen et al. | |
| 5,553,616 A | 9/1996 | Ham et al. | |
| 5,601,079 A | 2/1997 | Wong et al. | |
| 5,615,673 A | 4/1997 | Berger et al. | |
| 5,776,059 A | 7/1998 | Kaestle et al. | |
| 5,827,181 A | 10/1998 | Dias et al. | |

(Continued)

FOREIGN PATENT DOCUMENTS

EP    0 247 777(A1)    12/1987

(Continued)

OTHER PUBLICATIONS

E. E. Lawson et al., "Biomedical Applications of Raman Spectroscopy", Journal of Raman Spectroscopy, (1997) vol. 28, pp. 111-117.

(Continued)

*Primary Examiner*—Eric F. Winakur
(74) *Attorney, Agent, or Firm*—Gates & Cooper LLP (57) ABSTRACT

Disclosed are a device and methods for obtaining signals related to blood analytes and bone features by collecting spectra, such as fluorescence and Raman spectra, through the nail of a finger or toe. The invention additionally provides methods of modulating blood flow in a tissue of a subject.

17 Claims, 6 Drawing Sheets

U.S. PATENT DOCUMENTS

| | | | | |
|---|---|---|---|---|
| 5,830,132 A | * | 11/1998 | Robinson | 600/310 |
| 5,836,317 A | | 11/1998 | Kunst | |
| 6,070,093 A | * | 5/2000 | Oosta et al. | 600/316 |
| 6,289,230 B1 | * | 9/2001 | Chaiken et al. | 600/316 |
| 6,697,665 B1 | * | 2/2004 | Rava et al. | 600/475 |

FOREIGN PATENT DOCUMENTS

| | | |
|---|---|---|
| WO | WO 93/00856(A1) | 1/1993 |
| WO | WO 94/10901(A1) | 5/1994 |
| WO | WO 96/03074(A1) | 2/1996 |
| WO | WO 96/39926(A1) | 12/1996 |
| WO | WO 98/03847(A3) | 1/1998 |
| WO | WO 99/37205(A1) | 7/1999 |
| WO | WO 99/55222(A1) | 11/1999 |
| WO | WO 00/01295(A1) | 1/2000 |

OTHER PUBLICATIONS

Andrew J. Berger et al., "Multicomponent blood analysis by near-infrared Raman spectroscopy", Applied Optics, vol. 38, No. 13, May 1, 1999, pp. 2916-2926.

Andrew J. Berger et al., "Rapid, noninvasive concentration measurements of aqueous biological analytes by near-infrared Raman spectroscopy", Applied Optics, vol. 35, No. 1, Jan. 1, 1996, pp. 209-212.

M. Ries Robinson et al., "Noninvasive Glucose Monitoring in Diabetic Patients: A Preliminary Evaluation", Clin. Chem. 38/9, (1992) pp. 1618-1622.

Omar S. Khalil, "Spectroscopic and Clinical Aspects of Noninvasive Glucose Measurements", Clinical Chemistry 45:2, (1999) pp. 165-177.

* cited by examiner

METHOD OF TISSUE MODULATION FOR NONINVASIVE MEASUREMENT OF AN ANALYTE

This application claims the benefit of U.S. provisional patent application No. 60/220,144, filed Jul. 11, 2000, the entire contents of which are incorporated herein by reference. This application is related to U.S. patent application Ser. No. 09/349,061, filed Jul. 7, 1999, now U.S. Pat. No. 6,289,230, issued Sep. 11, 2001, and to U.S. Pat. No. 6,044,285, issued Mar. 28, 2000, and U.S. Pat. No. 6,223,063, issued Apr. 24, 2001, the entire contents of which are hereby incorporated by reference into this application.

Throughout this application various publications are referenced. The disclosures of these publications in their entireties are hereby incorporated by reference into this application in order to more fully describe the state of the art to which this invention pertains.

TECHNICAL FIELD OF INVENTION

The invention relates to a method of modulating blood flow in tissue. Mechanical pressure is applied to a nail, such as a fingernail or toenail, in order to affect the flow and presence of blood in the underlying tissue. The method facilitates the noninvasive measurement of analytes in blood and other tissues, particularly bone.

BACKGROUND OF THE INVENTION

There has long been considerable interest in the noninvasive monitoring of body chemistry. There are 16 million Americans with diabetes, all of whom would benefit from a method for noninvasive measurement of blood glucose levels. Using currently accepted methods for measuring blood glucose levels, many diabetics must give blood five to seven times per day to adequately monitor their health status. With a noninvasive blood glucose measurement, closer control could be imposed and the continuing damage, impairment and costs caused by diabetes could be minimized.

Blood oximetry is an example of an application of electronic absorption spectroscopy to noninvasive monitoring of the equilibrium between oxygenated and deoxygenated blood (U.S. Pat. No. 5,615,673, issued Apr. 1, 1997). Similarly, vibrational spectroscopy is a reliable mode of quantitative and qualitative ex vivo analysis for complex mixtures, and there are reports of in vitro applications of this method to metabolically interesting analytes (S. Y. Wang et al, 1993, Analysis of metabolites in aqueous solution by using laser Raman spectroscopy, Applied Optics 32(6):925–929; A. J. Berger et al., 1996, Rapid, noninvasive concentration measurements of aqueous biological analytes by near infrared Raman spectroscopy, Applied Optics 35(1):209–212). Infrared measures, such as vibrational absorption spectroscopy, have been applied to skin tissue, but with success limited by unavailability of suitable light sources and detectors at crucial wavelengths, and by heating of the tissue due to the absorption of incident radiation (U.S. Pat. No. 5,551,422, see also R. R. Anderson and J. A. Parrish, 1981, The Optics of Human Skin, J. Investigative Dermatology 77(1):13–19). Previous attempts to provide methods for noninvasive blood glucose monitoring are summarized in U.S. Pat. No. 5,553,616, issued on Sep. 10, 1996.

Optimal application of noninvasive techniques for blood analysis will requite improved methods for isolating signals attributable to blood versus surrounding tissues. Tissue modulation is an effective means of differentiating between mobile and static phases for in vivo spectroscopic applications. When the interest is specifically in the most mobile fluid, i.e. blood, then tissue modulation is essential for the application of vibrational spectroscopy. Earlier methods of tissue modulation based on application of mechanical pressure in such a manner as to affect blood flow by changing the pressure field driving the blood in the vasculature simultaneously with physically deforming the vasculature. This has the disadvantage of inducing small variability in the spectroscopic signals, partly due to the induction of actual small variations in the spectroscopic properties of the vasculature as well as that of the blood.

There is a continuing need to improve upon the process of tissue modulation and the invention disclosed herein teaches how to apply the pressure more precisely and perform the necessary optical tasks so as to maximize the blood tissue modulation while minimizing the spectroscopic variation of the background static tissues.

SUMMARY OF THE INVENTION

The invention provides a device and methods to meet this need for improved methods for obtaining signals related to blood analytes. The invention is based on the surprising discovery that direction of excitation light at the fingernail facilitates both the ability to modulate blood flow with greater precision and the ability to collect emitted spectra with decreased scattering losses. In addition, the methods of the invention provide an unexpected further capability for observing spectra associated with bone.

The invention provides a method of modulating blood flow in a tissue of a subject. The method comprises applying a tissue modulation device comprising a plate having an orifice to the tissue of the subject. In a preferred embodiment, the device is applied to a nail of the subject, such as a finger or toe nail. To obtain spectra of blood through the fingernail, the subject's fingernail is placed in juxtaposition with, but not touching, the orifice of the tissue modulation device. However, for the fingernail side, the "squeezed" or "blood depleted" state is what is achieved at that point. To achieve the "unsqueezed" or relatively blood replete state, the subject can use a finger on the other hand to push gently against the volar side of the fingertip, causing tie capillary bed to fill, as can be easily confirmed by visual observation of reddening of the nail area.

Blood flow to the region under the nail can be modulated through the use of directed pressure to block an artery and shunt the blood supply in a region distal to the site where pressure is applied. This means of directed blood flow avoids mechanical deformation of the zone being probed spectroscopically. To obtain good tissue modulated blood Raman spectra, one can direct the excitation light through the fingernail at the approximate middle of the nail, usually a few to several millimeters above the umbra, on the approximate bilateral symmetry plane of the nail. The region being examined or probed is the region between the distal phalanx and the nail bed inclusive. Without placing pressure on the nutrient supply to the epiphysis, there is normally a slight blanch, i.e. blood depletion, under the nail in the region specified. Placing pressure on the volar side of the finger, near the joint such that the upper branch of the nutrient flow to the epiphysis is blocked, shunts blood arriving via the proper palmar digital artery from the volar side of the finger, i.e. the nutrient branches of the metaphysis into the sublingual space under the nail specified above.

Blood flow can also be modulated through the use of temperature. Because blood can serve as a heat dissipator, heat accumulator and overall heat moderator, one can apply heat or cold to a region of a subject and alter the blood supply. For example, one can contact the hand of a subject with a heat source, such as a warm glove, and cause more blood flow to the hand.

The invention further provides a method of noninvasive spectroscopic measurement of an analyte in a subject. The method comprises irradiating the tissue in a blood-replete state with electromagnetic radiation having an excitation wavelength, wherein the tissue is irradiated by passing light through an orifice in a plate and through a nail of the subject. The method further comprises collecting the spectra emitted by the tissue in the blood-replete state. The method further comprises irradiating the tissue in a blood-depleted state with electromagnetic radiation having an excitation wavelength, and collecting the spectra emitted by the tissue in the blood-depleted state. The collected spectra are then analyzed to determine a concentration of analyte present in the tissue. The analyzing comprises determining the difference between the spectra collected in the blood-replete and blood-depleted states. The spectra are preferably Raman spectra. Examples of other spectra include, but are not limited to, NMR, ESR, UV visible absorption, IR absorption, fluorescence and phosphorescence spectra. In a typical embodiment, spectra indicative of blood volume (e.g., fluorescence, phosphorescence, absorption) are used to normalize signals associated with the analyte of interest to blood volume.

DETAILED DESCRIPTION

Tissue modulation refers to manipulating the tissue to which the method is applied so that measurements, such as spectroscopic measurements, can be made in both blood replete and blood depleted states. One strategy for tissue modulation is the application of pressure to an area of tissue, such as a finger tip. The difference between measurements taken in the blood replete and blood depleted states provides a measure indicative of components in the blood while minimizing the effects of extraneous spectroscopic signals due to calluses, dirt, soap residue and other sources associated with the surrounding tissue. When tissue modulation is employed during noninvasive spectroscopy, for example, the analysis can include determining the difference between the spectra collected in the blood replete and blood depleted states.

The invention disclosed herein is based on the surprising discovery that direction of excitation light at the fingernail facilitates both the ability to modulate blood flow with greater precision and the ability to collect emitted spectra with decreased scattering losses. This provides a very clean modulation of blood and has the added advantage of viewing the tissue through the nail. The superior transparency and smoothness of the nail compared to the skin and stratum corneum almost everywhere else on the body greatly decreases scattering losses and therefore gives more reliable spectroscopic data. In addition, the methods of the invention provide an unexpected further capability for observing spectra associated with bone.

Definitions

All scientific and technical terms used in this application have meanings commonly used in the art unless otherwise specified. As used in this application, the following words or phrases have the meanings specified.

As used herein, "tissue" means any portion of an organ or system of the body, including, but not limited to, skin, capillary beds, blood, muscle, breast and brain.

As used herein, "Raman spectra associated with" a given component refers to those emitted Raman spectra which one skilled in the art would attribute to that component. One can determine which Raman spectra are attributable to a given component by irradiating that component in a relatively pure form, and collecting and analyzing the Raman spectra emitted by the component in the relative absence of other components.

As used herein, "blood replete" refers to a state in which blood flow through a tissue is unobstructed by, for example, vasoconstriction induced by cooling or the application of pressure. The blood replete state can be enhanced by conditions which increase vasodilation, such as warming.

As used herein, "blood depleted" refers to a state in which blood flow through a tissue is substantially restricted and blood volume is minimized. A blood depleted state can be achieved by, for example, cooling and/or applying pressure to the tissue.

As used herein, "opaque" refers to the optical property of an object such that light is substantially prevented from passing through the object. In preferred embodiments of the tissue modulation device, no light passes through the opaque regions.

As used herein, "optically transparent" refers to the optical property of an object such that light is permitted to pass through the object.

As used herein, "portion of tissue" refers to an area of tissue that light penetrates, and from which a signal is collected.

Overview

Figure 1:
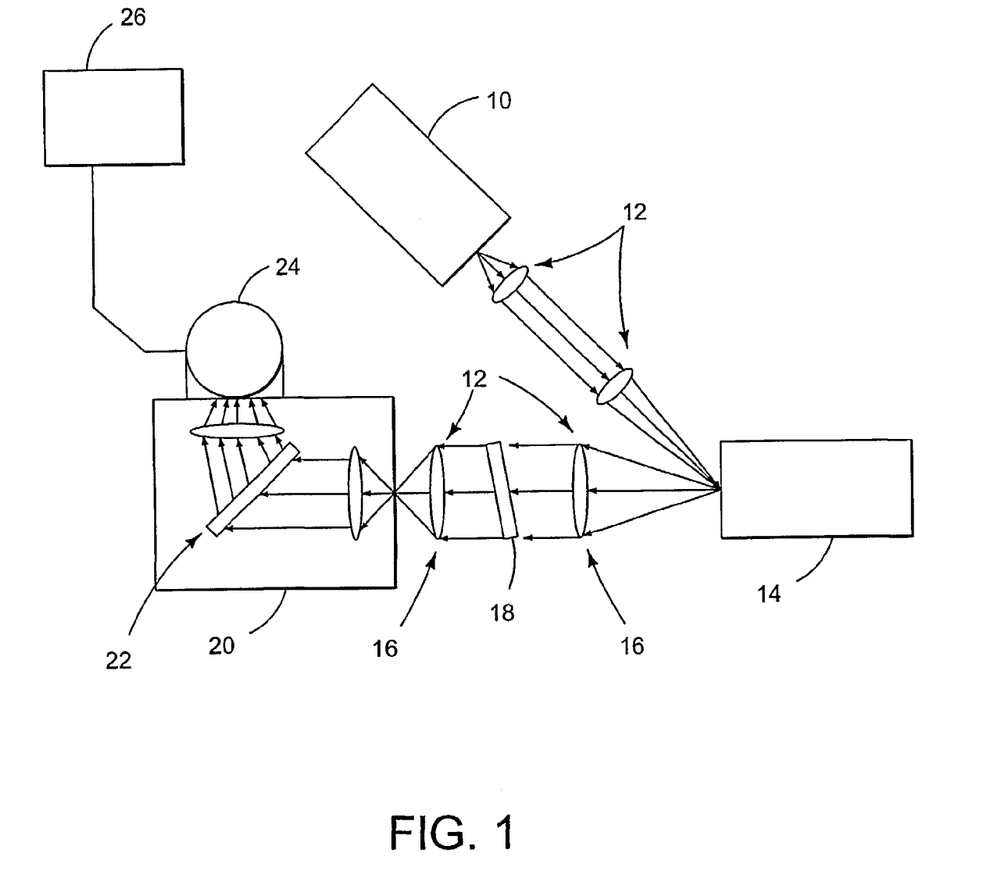
FIG. 1 is a schematic diagram of an optical layout for use in accordance with the invention.

Two representative devices for use with the methods of the invention are described herein. Those skilled in the art will appreciate that a variety of suitable modifications and substitutions can be made. A schematic diagram of one of the optical set ups is shown in FIG. 1. In both systems an amplitude and wavelength stabilized, external cavity, CW laser 10, (785 nm with the Kaiser spectrograph and 805.6 nm with the Process Instruments spectrograph, Process Instruments, Salt Lake, Utah) produces a maximum total usable power of about 300 mW. The laser 10 is filtered through a dielectric stack (Omega Optical, Brattleboro, Vt.) bandpass filter having an optical density ratio between the center at 785 nm and about 600 cm$^{-1}$ to the red of about 5.

In both systems, optics for correcting the spatial arrangement of the fast and slow axes of the laser divergence, as well as for obtaining the optimum polarization for diffraction efficiency and background reduction in the f1.4 holographic spectrograph 20, (Holospec, Kaiser, Ann Arbor, Mich.) eventually allow one to bring as much as ≈150 mW of laser power to the sample. All measurements are made with 100 mW focused to a spot at the surface of the stratum corneum of about 2 mm. The spectrograph 20 includes a holographic transmission grating 22.

All optics are antireflection coated for 785 nm (or 805.6 as appropriate to the equipment in use) and a 13 cm focal length lens 12 is used to finally bring the light to the tissue of interest, which is positioned in a tissue modulator 14. An angle of incidence of approximately 53° gives acceptable results. For both systems, the light collection system uses two simple plano-convex lenses 16 and a holographic notch filter 18 (Kaiser). The Kaiser based system also employs a Polacor (Corning) polarizer in the optical train bringing the scattered light from the sample to the entrance of the spectrograph 20. The detection system of the Kaiser based system is an IR enhanced, liquid nitrogen cooled CCD array 24 from Princeton Instruments. The resolution of this spectrograph system is ≈6 cm$^{-1}$ with wavenumber accuracy of about ±6 cm$^{-1}$ using a calibration based on known lines in atomic emission spectra. Data from the CCD camera 24 is sent to a computer 26.

The other system, which is much smaller and has a total cost of about half the original device, differs in the choice of spectrograph 20, detector 24 and optics in the signal collection train. In this case an Andor CCD detector 24 (Andor Technologies, Belfast, Ireland), Peltier cooled and coupled to a Process Instruments f2.1 grating spectrograph 20 is employed. The pair of light collection lenses focuses the Rayleigh rejected light into a fiber bundle that is reconfigured into a line image as it is coupled to the spectrograph 20.

Figure 2:
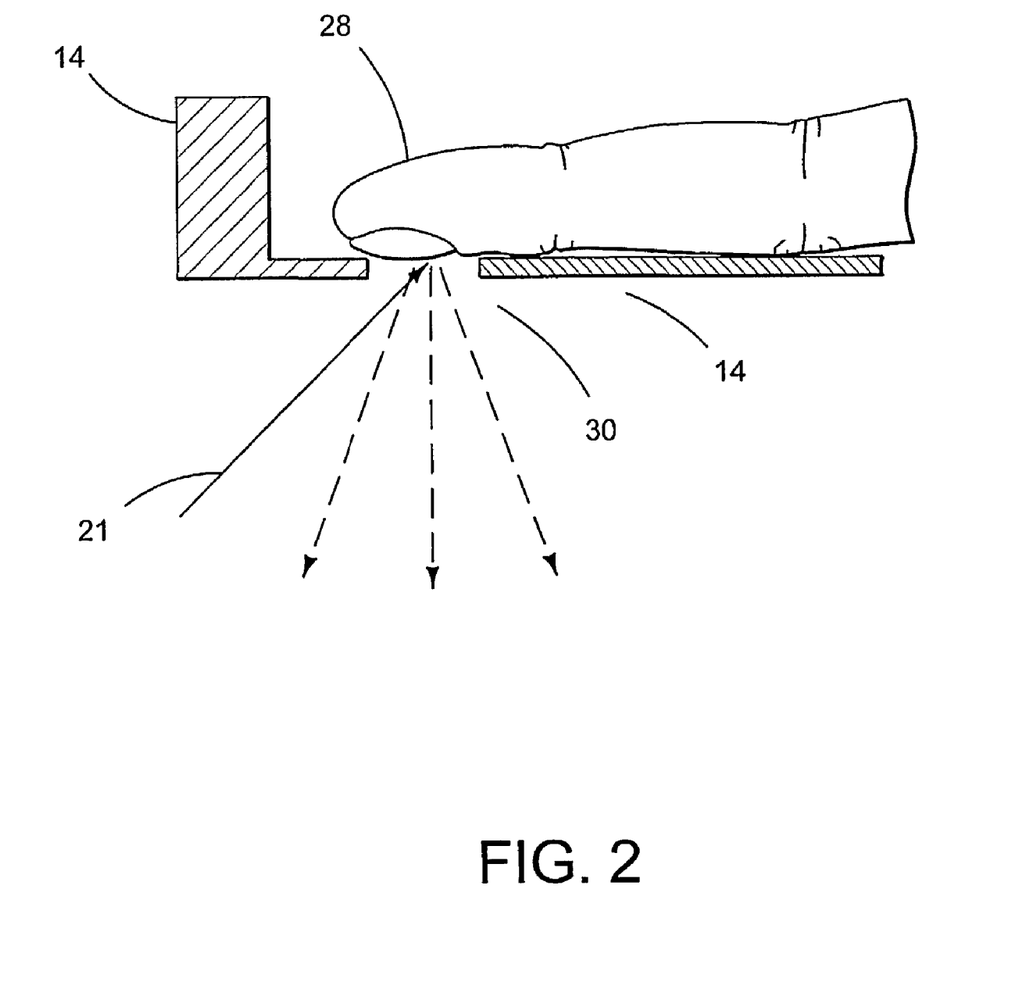
FIG. 2 is a schematic diagram of a fingernail positioned at the orifice of the tissue modulator.
Figure 3:
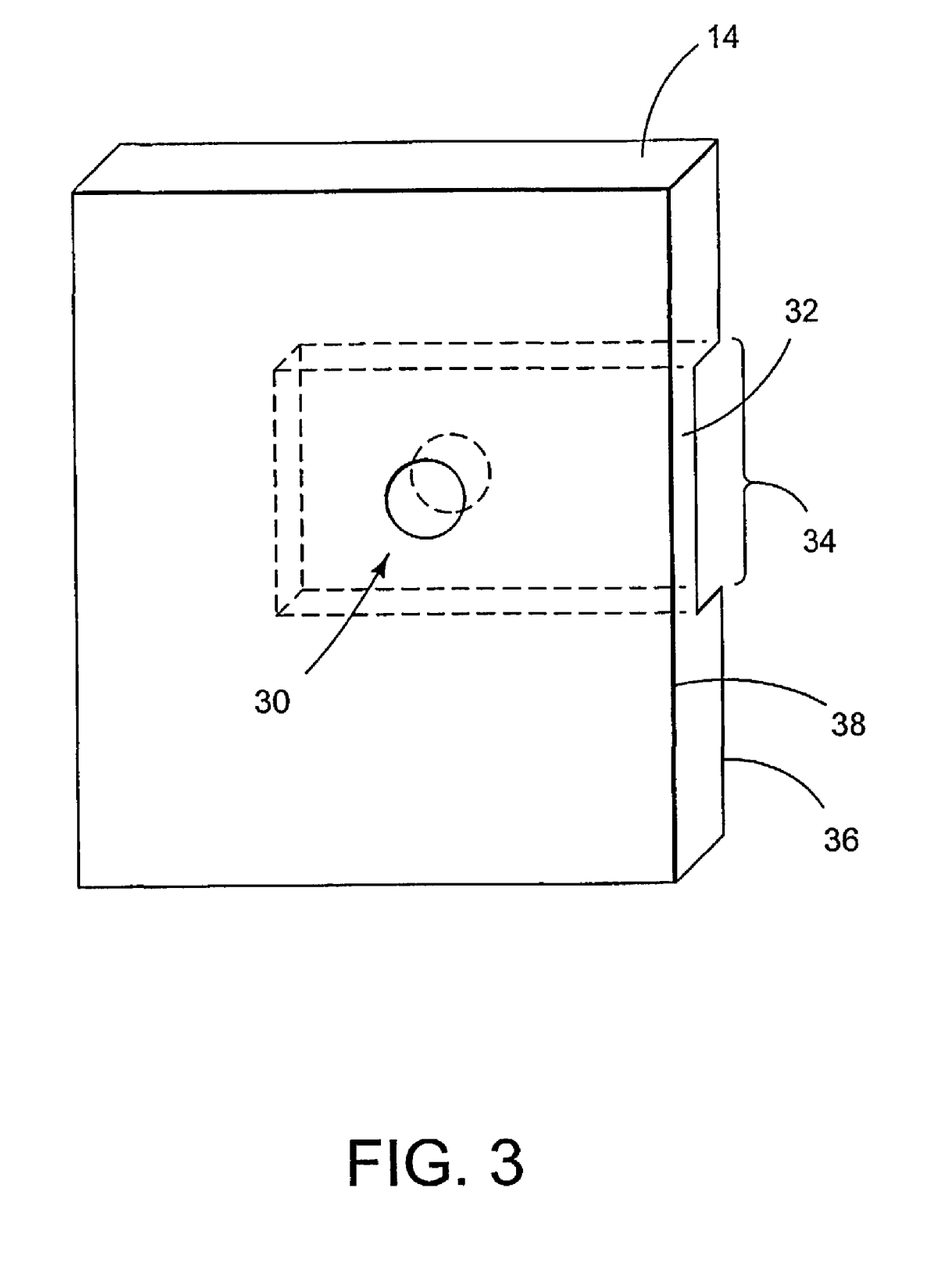
FIG. 3 is a schematic diagram of a tissue modulator.

For both instruments, the sample holder itself, or "tissue modulator" 14, as shown in FIG. 3, contains an orifice 30 in a 1 mm thick aluminum plate 32. The fingertip 28 is placed with respect to the plate 32 so that the tissue to be interrogated is accessible to the excitation light 21 through the orifice 30 (FIG. 2). When the volar side of the finger is simply placed in sample holder, without any pressure between the finger 28 and the orifice 30, so that the subject can just feel the circle of the metal edge against his/her fingertip, the finger 30 is in the "unsqueezed" state. In this state, the blood volume is normal and the flow patterns and net rate into and out of the region is normal. When the subject presses the finger 28 against the orifice 30, the pressure on the exposed fingertip 28 is increased, and at equilibrium, the blood content of those tissues in the region inside the orifice 30 is changed, i.e. modulated, to the "squeezed" state.

To achieve good mechanical pressure modulation, the total pressure involved varies somewhat from sample to sample but is typically less than 1 Newton. To obtain spectra of blood through the fingernail, the subject places the fingernail in juxtaposition with, but not touching, the same orifice 30. However, for the fingernail side, the "squeezed" or "blood depleted" state is what is achieved at that point. To achieve the "unsqueezed" or relatively blood replete state, the subject uses a finger on the other hand to push gently against the volar side of the fingertip, causing the capillary bed to fill, as can be easily confined by visual observation. Different sized and shaped orifices are optimal for different size fingers and different types of tissue modulation. For the data described herein, a single round orifice 0.95 cm in diameter was used for all the subjects and the average finger was 5.3 cm in circumference.

Methods of the Invention

The invention provides a method of measurement of blood volume simultaneously with measurements of a signal or signals indicative of one or more blood analytes. The blood volume measurement permits normalization of blood analyte measurements to allow computation of concentration levels. Temperature and pressure can be used to affect the capillary content and, although these can be controlled to a large extent, it is desirable to use tissue modulation apparatus to aid in the normalization. The invention provides a method for normalization that is less vulnerable to error due to differences between individual anatomy and blood flow patterns.

The invention provides a method of noninvasive spectroscopic measurement of an analyte in a subject. In one embodiment, the method comprises applying tissue of the subject to a tissue modulation device 14 so that blood flow is minimized in the tissue and the tissue alternates between a blood-depleted state and a blood-replete state. Alternatively or additionally, one can induce or enhance the blood-depleted and blood-replete states through other methods of tissue modulation, such as applying pressure to shunt blood flow, or applying heat or cold to direct blood flow as desired.

The method further comprises irradiating the tissue in a blood-replete state with electromagnetic radiation having an excitation wavelength and collecting the spectra emitted by the tissue in the blood-replete state. The method further comprises irradiating the tissue in a blood-depleted state with electromagnetic radiation having an excitation wavelength and collecting the spectra emitted by the tissue in the blood-depleted state. The method additionally comprises analyzing the collected spectra to determine a concentration of analyte present in the tissue, wherein the analyzing comprises determining the difference between the spectra collected in the blood-replete and blood-depleted states. Examples of spectra that can be collected include, but are not limited to, Raman, nuclear magnetic resonance NMR), electron spin resonance (ESR), UV visible absorption, infrared absorption, optical rotary dispersion, polarimetry, circular dichioism, fluorescence and phosphorescence spectra. In a typical embodiment, spectra indicative of blood volume (e.g., fluorescence, phosphorescence, absorption) are used to normalize signals associated with the analyte of interest to blood volume.

The tissue to be probed in the methods of the invention has an ample supply of blood circulating in capillary beds, such as the fingertip or toe, and the blood flow in the finger or toe is modulated by applying pressure to the nail, or more preferably, to the volar region of the finger remote to the nail. The excitation light, and emitted spectra, pass through the nail to, and from, the well-vascularized underlying nail bed.

The subject is preferably a vertebrate, such as a mammal, bird, reptile or fish. Examples of mammals include, but are not limited to, human, bovine, porcine, ovine, murine, equine, canine, and feline. In a most preferred embodiment, the subject is human. The method is suitable for use with humans of any age or size, such as newborns, infants, children, and adults. Use of a toe nail may be preferred when the subject is an infant or for subjects whose fingernails are not reasonably accessible.

Figure 5:
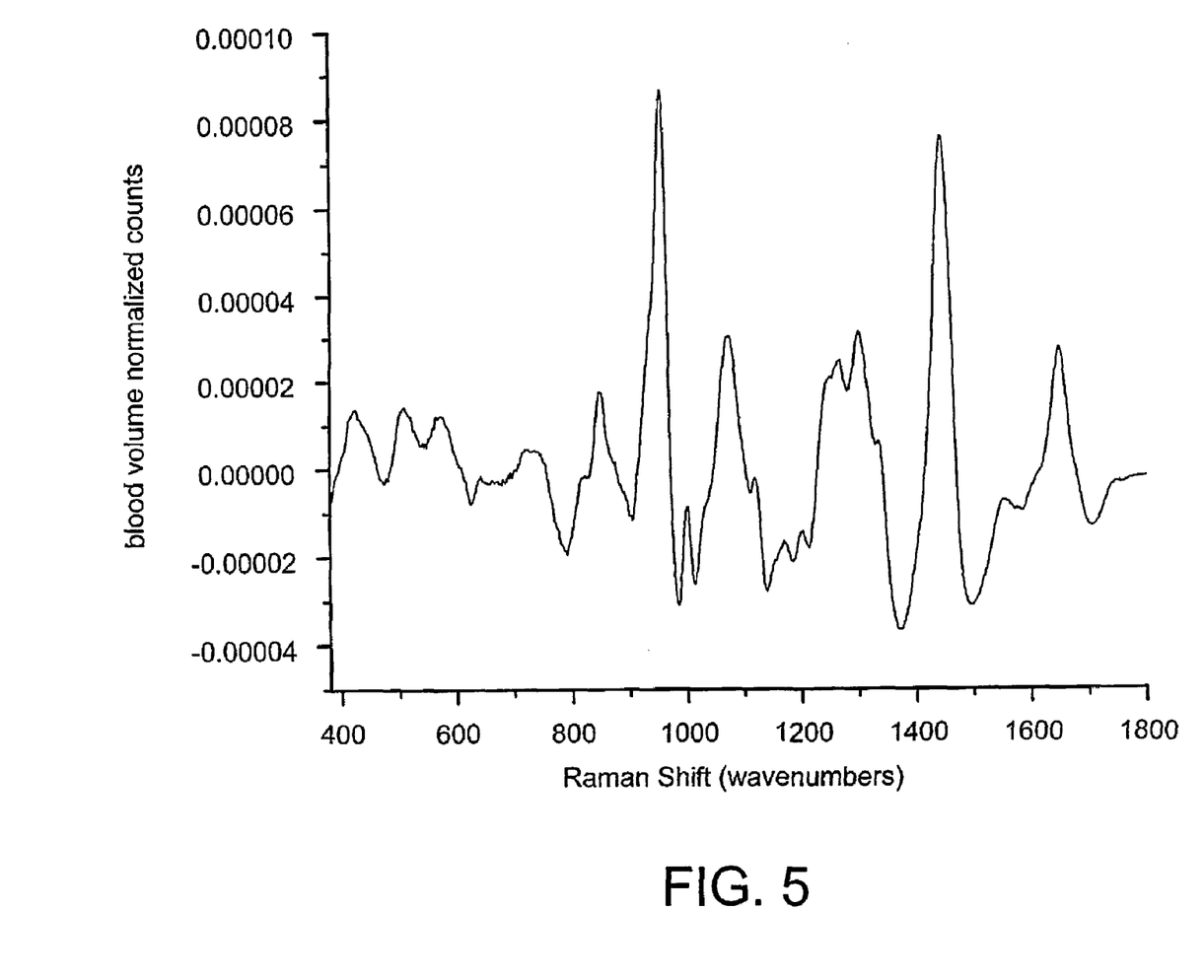
FIG. 5 is a Raman spectrum of blood collected through the nail bed matrix, plotted as normalized counts representing blood volume versus Raman shift, in wavenumbers. A strong hydroxyapatite P—O stretch is apparent at 963 $cm^{-1}$.

In one embodiment, the collected spectra are analyzed for a feature associated with bone, such as hydroxyapatite. Hydroxyapatite is a complex phosphate of calcium, and a mineral that serves as the chief structural element of vertebrate bone. A strong hydroxyapatite P—O stretch is apparent at 963 cm$^{-1}$ (FIG. 5). This feature can be analyzed and used to determine relative changes or deficiencies in bone density, for example, providing a screening or diagnostic tool for the detection and monitoring of a bone condition such as osteoporosis and its response to treatment. Blood flow manipulations can be used to provide an index matching fluid, thereby facilitating the observation of bone features. Because the index of refraction for bone is higher than the index of refraction for blood (approximately 1.35), light penetration to the bone (e.g., distal phalanx under the fingertip) is facilitated. When blood is depleted from the nail bed, a reflection off the bone is obtained. When the nail bed is replete with blood, however, light entering the fingertip must cross two interfaces, facilitating penetration to the bone and the ability to obtain a clear bone-related signal.

Tissue Modulation Device

The invention disclosed herein provides a device 14 that can be used for modulating blood flow in a tissue (FIG. 3). The device 14 is suitable for use in conjunction with methods for measuring an analyte in the tissue. The device 14 can be used noninvasively. The device 14 comprises an upper surface 36 and a lower surface 38, and an orifice or channel passing through the upper 36 and lower 38 surfaces of the device 14. In some embodiments, a lens or other optically transparent element is positioned within the orifice 30 or channel. Preferably, a portion of the device 14 is recessed relative to the remainder of the device 14 so as to provide a guide 34 or channel in which a subject's finger or toe can be positioned over the orifice 30 as shown in FIG. 2. Preferably, the guide is adapted to provide a gap or ridge or other modification to stabilize the positioning of the finger (or toe), thereby minimizing movement.

In preferred embodiments, the orifice 30 is less than about 1 cm in diameter, but may range from about 2.5 mm to about 1.5 cm. More preferably, the diameter of the orifice 30 is about 0.9 to about 0.95 cm in diameter. The diameter may need to be larger or smaller to accommodate infants, children or subjects with particularly small or large fingers. The shape and size of the orifice 30 can be adapted for different size fingers or toes, and for different types of tissue modulation. The thickness between the upper surface 36 and the lower surface 38 of at least a portion of the device 14 is preferably less than about 3 mm, more preferably about 1 mm.

The device 14 can be optically coupled with a source of electromagnetic radiation and/or with a light detector. In one embodiment, the device 14 includes a light collection system, which can include one or more lenses. In a preferred embodiment, a lens or other light collection system is integrated into the orifice 30 or channel of the device 14. In another embodiment, the device 14 is part of an apparatus or system that additionally includes means for irradiating the tissue with a light source and/or means for collecting and detecting light emitted by the irradiated tissue. One or more beamsplitters and additional lenses, filters and collimators can be introduced into the light path to modify the light entering and or exiting the tissue.

Preferably, the signals are subtracted while in the analog domain, prior to signal digitization or amplification. This affords improved signal to noise and dynamic range compared to that obtainable by amplifying and digitizing the signals emanating from the blood depleted or blood replete tissue prior to signal subtraction. One advantage to subtracting the signals prior to digitization is that each detector is on the same substrate and therefore biased by the same power supply such that the noise associated with environmental fluctuations and the power supply are the same for each detector. The noise is then removed by simple analog subtraction. Because they can be integrated on the same "chip", the detectors and the amplification/subtraction circuitry can be designed and fabricated to share components such as load resistors in amplifiers, so that much of the noise present in the electrical currents produced by these different detectors is correlated. The noise can then be filtered out directly, and amplification of the noise prior to subtraction is avoided. Digitizing and then subtracting noise would lead to an increase in noise in the difference between the signal from a blood replete zone and the signal from a blood depleted zone.

The approach described above achieves a rejection of background light from the primary light source, a tissue modulated spectroscopic signal, and an automatic analog processing of the signal to minimize noise and increase signal.

EXAMPLES

The following examples are presented to illustrate the present invention and to assist one of ordinary skill in making and using the same. The examples are not intended in any way to otherwise limit the scope of the invention.

Example 1

Fluorescence Spectra Obtained Through Nail Reflect Blood Volume Fluctuations with Tissue Modulation When the tissue, i.e. a fingertip oriented either volar or nail side first, is placed in the apparatus as described above, and irradiated at 785 or 830 nm, the raw spectroscopic response is a broad featureless fluorescence emission 1 from all the tissues present with Raman features superimposed on top. The raw spectral features of blood, fluorescence and Raman, are obtained by subtracting a blood-depleted spectrum from a blood rich spectrum. The Raman and fluorescence contained in this raw difference spectrum can be isolated by various statistically unbiased procedures but we uniformly perform the following processing. The raw difference spectrum below 210 cm$^{-1}$ is discarded and the remaining data is smoothed using a standard commercially available 101 point adjacent averaging smoothing routine. The smoothed raw difference spectrum is subtracted from the raw difference data and a representation of the Raman spectrum is obtained. This part of the procedure induces some negative lobes in the Raman spectrum for reasons which are well known and easy to understand, but it also provides a uniform statistically unbiased approach for comparing the spectra. Other techniques such as piecewise linear baseline subtraction, or polynomial fitting based schemes can also be used with essentially identical results in all the cases tried, however these other techniques introduce their own types of artifacts. A 7 point adjacent smoothing routine is applied to the isolated Raman spectrum for display purposes. Finally, the raw difference spectrum is integrated to obtain a measure of the total fluorescence.

Figure 4A:
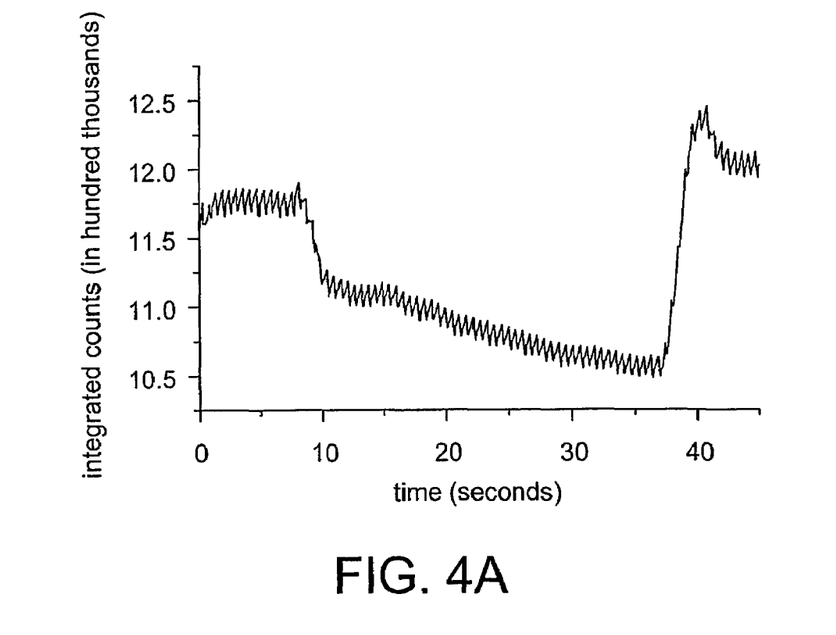
FIGS. 4A–B are graphs showing integrated fluorescence as a function of time and pressure for measurements taken from the volar side (FIG. 4A) and the fingernail side (FIG. 4B) of the finger. In each case, the pressure was applied at approximately 8 seconds, and was subsequently released at about 30 seconds.
Figure 4B:
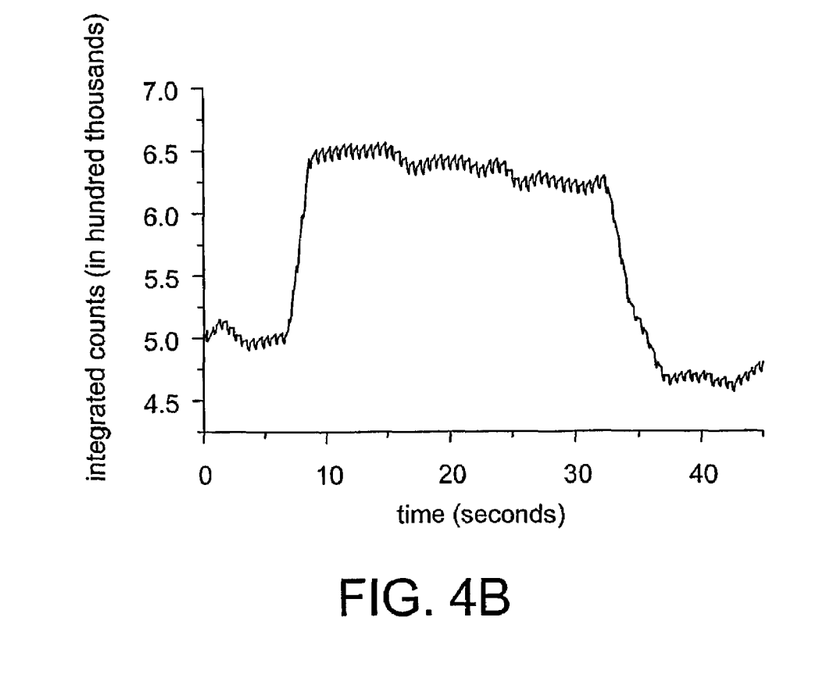

FIGS. 4A–B show the response of the total integrated fluorescence obtained through either the volar side or the fingernail side of the same finger tip under appropriate tissue modulation conditions, i.e. pressing and unpressing. The rise or fall of the average fluorescence tracks the easily observed visual response, i.e. blanching or "pinking" of the capillary beds to the mechanical stimulation. The pinker the tissue/capillary bed, the more fluorescence. Because "pressing" has the opposite effect on blood depletion for the volar versus nail sides of the finger, the data shown in FIGS. 4A and 4B show responses in opposing directions during the pressing portion of the measurement.

Example 2

Raman Spectra Obtained Through Nail Include a Strong Bone-Related Feature

Raman spectra collected through the nail bed of a finger ate useful not only because of the ease with which one can modulated the blood flow by applying pressure to the volar side and/or occluding the nutrient branch of the metaphysis, but also because of the ability to rather clearly identify specific Raman features. For example, FIG. 5 is a Raman spectrum of blood collected through the nail bed matrix, plotted as normalized counts representing blood volume versus Raman shift, in wavenumbers. A strong hydroxyapatite P—O stretch is apparent at 963 $cm^{-1}$. This hydroxyapatite feature is indicative of bone and can be used to assess bone density.

Example 3

Figure 6:
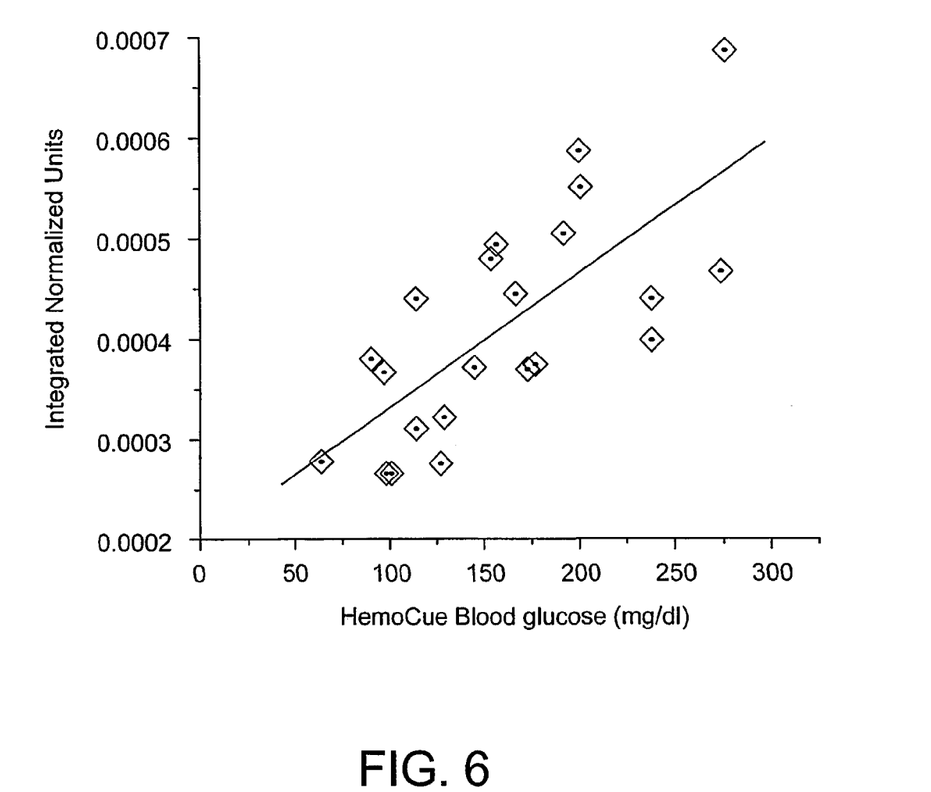
FIG. 6 is a graph depicting the correlation between noninvasive, tissue modulated Raman spectroscopic glucose measurements taken through the fingernail, plotted as integrated normalized units, and HemoCue fingerstick glucose measurements, in mg/dl, for 23 individuals (R=0.74, n=23, p<0.0001).

Blood Glucose Measurements Based on Raman Spectra Obtained Through Nail Correlate with Conventional Fingerstick Glucose Measurement FIG. 6 is a graph depicting the correlation between noninvasive, tissue modulated Raman spectroscopic glucose measurements taken through the fingernail, plotted as integrated normalized units, and HemoCue fingerstick glucose measurements, in mg/dl, for 23 individuals (R=0.74, n=23, p<0.0001). These are the results of clinical tests on 23 different individuals in which the measurements were made through the fingernail using the Kaiser-Princeton based instrument. The correlation of 0.74 is essentially equal to the results of random testing using volar side measurements as determined previously. The fingernail data accumulation time was 200 total seconds (100 sec pressed+100 seconds unpressed for all of the points although tracking data was taken using a total accumulation time of either 200 or 100 seconds. In testing subjects, hemoglobin and glucose measurements were made using appropriate HemoCue devices and standard fingersticks. All studies were approved by appropriate institutional review and all participants gave informed consent.

Those skilled in the art will appreciate various modifications that can be made to the specific embodiments described and that are within the scope of the invention.

What is claimed is:

1. A method of noninvasive spectroscopic measurement of an analyte in a subject comprising:
   (a) irradiating tissue of the subject through a nail with electromagnetic radiation having an excitation wavelength while the tissue is in a blood-replete state;
   (b) collecting the Raman spectra emitted by the tissue in the blood-replete state;
   (c) applying a tissue modulation device having an orifice to the nail of the subject so as to achieve a blood-depleted state within the tissue;
   (d) irradiating the tissue through the nail with electromagnetic radiation having an excitation wavelength while the tissue is in the blood-depleted state;
   (e) collecting the Raman spectra emitted by the tissue in the blood-depleted state; and
   (f) analyzing the collected Raman spectra to determine a concentration of analyte present in the tissue, wherein the analyzing comprises determining the difference between the Raman spectra collected in the blood-replete and blood-depleted states.

2. The method of claim 1, wherein the nail is a fingernail.

3. The method of claim 1, wherein the nail is a toenail.

4. The method of claim 1, wherein the analyte comprises glucose.

5. The method of claim 1, wherein the analyte comprises hydroxyapatite.

6. The method of claim 1, wherein the blood-replete stare is achieved by hindering blood flow through an artery that serves the tissue.

7. The method of claim 1, wherein the blood-replete state is achieved by altering the temperature of the tissue.

8. The method of claim 7, wherein the temperature is altered by heating.

9. The method of claim 7, wherein the temperature is altered by cooling.

10. A method of noninvasive spectroscopic measurement of an analyte in a subject comprising:
    (a) irradiating tissue of the subject through a nail with electromagnetic radiation having an excitation wavelength by directing the electromagnetic radiation at the nail side of the finger or toe of the subject;
    (b) collecting the spectra emitted by the tissue through the nail side of the finger or toe of the subject in blood-replete and blood-depleted states;
    (c) analyzing collected Raman spectra to determine a signal that is proportional to the amount of analyte present in the tissue by determining the difference between Raman spectra collected in the blood-replete state and the blood-depleted state;
    (d) analyzing spectra collected in step (b) that are indicative of blood volume; and
    (e) comparing the spectra analyzed in step (c) with the spectra analyzed in step (d) to determine the amount of analyte per unit blood volume.

11. The method of claim 10, wherein the spectra indicative of blood volume comprise fluorescence, phosphorescence or absorption spectra.

12. The method of claim 10, wherein the nail is a fingernail.

13. The method of claim 10, wherein the nail is a toenail.

14. The method of claim 10, wherein the analyte comprises glucose.

15. The method of claim 10, wherein the analyte comprises hydroxyapatite.

16. The method of claim 10, wherein the blood-replete state is achieved by hindering blood flow through an artery that serves the tissue.

17. The method of claim 10, wherein the blood-replete state is achieved by altering the temperature of the tissue.

* * * * *

UNITED STATES PATENT AND TRADEMARK OFFICE
CERTIFICATE OF CORRECTION

| | | |
|---|---|---|
| PATENT NO. | : 7,050,842 B2 | Page 1 of 1 |
| APPLICATION NO. | : 10/332748 | |
| DATED | : May 23, 2006 | |
| INVENTOR(S) | : Joseph Chaiken et al. | |

It is certified that error appears in the above-identified patent and that said Letters Patent is hereby corrected as shown below:

Column 10, line 20, claim 6, "stare" should read --state--.

Signed and Sealed this

Twelfth Day of September, 2006

JON W. DUDAS
*Director of the United States Patent and Trademark Office*